United States Patent
Tseng et al.

(10) Patent No.: US 11,439,355 B2
(45) Date of Patent: Sep. 13, 2022

(54) PERTURBATION-INJECTION-LOCKED PHYSIOLOGICAL SIGNAL SENSOR

(71) Applicant: National Taiwan University of Science and Technology, Taipei (TW)

(72) Inventors: Chao-Hsiung Tseng, New Taipei (TW); Cheng-Zhou Wu, Tainan (TW)

(73) Assignee: NATIONAL TAIWAN UNIVERSITY OF SCIENCE AND TECHNOLOGY, Taipei (TW)

( * ) Notice: Subject to any disclaimer, the term of this patent is extended or adjusted under 35 U.S.C. 154(b) by 407 days.

(21) Appl. No.: 16/851,443

(22) Filed: Apr. 17, 2020

(65) Prior Publication Data
US 2021/0244363 A1     Aug. 12, 2021

(30) Foreign Application Priority Data

Feb. 10, 2020  (TW) .................................. 109104013

(51) Int. Cl.
| | | |
|---|---|---|
| *A61B 5/0205* | (2006.01) |
| *A61B 5/024* | (2006.01) |
| *A61B 5/00* | (2006.01) |
| *A61B 5/08* | (2006.01) |

(52) U.S. Cl.
CPC .......... *A61B 5/7228* (2013.01); *A61B 5/0205* (2013.01); *A61B 5/02427* (2013.01); *A61B 5/6824* (2013.01); *A61B 5/6826* (2013.01); *A61B 5/7225* (2013.01); *A61B 5/0816* (2013.01)

(58) Field of Classification Search
CPC . A61B 5/0205; A61B 5/02427; A61B 5/6824; A61B 5/6826; A61B 5/7225; A61B 5/7228
See application file for complete search history.

(56) References Cited

U.S. PATENT DOCUMENTS

2017/0135600 A1* 5/2017 Chien .................. A61B 5/7207
2019/0298234 A1* 10/2019 Omenetto .......... A61B 5/14532

OTHER PUBLICATIONS

Baker, E et al., "Passive Split Ring Resonator for Continuous Physiological Sensing Through Conductivity Measurements," Proceedings of the ASME 2013 International Mechanical Engineering Congress and Exposition, ASME, 2013. (Year: 2013).*
Baghelani, M et al., "Non-invasive continuous-time glucose monitoring system using a chipless printable sensor based on split ring microwave resonators," Scientific Reports, (2020) 10:12980. (Year: 2020).*
Wu, Cheng-Zhou et al. (2019). A Perturbation-Injection-Locked Sensor with Self-Oscillating Active CSRR for Vital-Sign Detection from Fingertip. Conference: 2019 IEEE/MTT-S International Microwave Symposium—IMS 2019. Jun. 2019. pp. 369-372. 10.1109/MWSYM.2019.8700980.

* cited by examiner

*Primary Examiner* — Eric F Winakur
(74) *Attorney, Agent, or Firm* — WPAT, PC

(57) ABSTRACT

A physiological signal sensor, comprising a self-oscillating complementary split-ring resonator (SO-CSRR), a demodulator and a microcontroller (MCU). The SO-CSRR detects a physiological signal and outputs a modulated signal, the demodulator receives the modulated signal and outputs a pulse physiological signal, the baseband amplifier receives the pulse physiological signal and outputs an amplified pulse physiological signal, and the MCU receives the amplified pulse physiological signal and outputs a digital signal.

10 Claims, 5 Drawing Sheets

PERTURBATION-INJECTION-LOCKED PHYSIOLOGICAL SIGNAL SENSOR

CROSS REFERENCE TO RELATED APPLICATION

This application claims the benefits of Taiwan application Serial No. 109104013, filed on Feb. 10, 2020, the disclosures of which are incorporated by references herein in its entirety.

FIELD

The present disclosure relates in general to a physiological signal sensor and, particular, to a perturbation and injection-locked theories based physiological signal sensor.

BACKGROUND

Physiological signals can be measured and used to evaluate a person status. For example, heart beats, finger pulse, respiration, body temperature, blood pressure and etc. are signals that can be used to evaluate whether a person shows vital sign, or to evaluate a person's health status.

With the rapid development in the field of wearable devices and health care, more and more wearable devices are equipped with one or more physiological signal detection functions. For example, some wearable devices are capable of measuring wearers' electrocardiography (ECG or EKG) so as to obtain wearers' heart beats data. Recently, watches that are capable of measuring wrist pulse signals can further be seen on the market. These watches are equipped with photoplethysmography (PPG) sensors, which are sensors that obtain heart beats data through measuring pulse signals from the wrist.

However, physiological signals are generally weak signals, and this property makes physiological signals difficult to be detected. If physiological signals are further interferes by noises, detection can be further difficult. In addition to the foregoings, PPG can be affected by other factors such as wearable device being wore too tight or too loose, ambient light, skin property and etc.

Therefore, how to effectively detect/measure physiological signals and how to effectively process and analyze these signals become more and more critical in relevant fields.

SUMMARY OF THE DISCLOSURE

An object of the present disclosure is to provide a physiological signal sensor. The physiological signal sensor includes a self-oscillating complementary split-ring resonator (SO-CSRR) element, a demodulator, a baseband amplifier, and a microcontroller (MCU). The SO-CSRR element is configured to detect a physiological signal and output a modulated signal, the demodulator receives the modulated signal and outputs a pulse physiological signal, the baseband amplifier receives the pulse physiological signal and outputs an amplified pulse physiological signal, and the MCU receives the amplified pulse physiological signal and outputs a digital signal.

BRIEF DESCRIPTION OF THE DRAWINGS

The present disclosure will become more fully understood from the detailed description given herein below and the accompanying drawings which are given by way of illustration only, and thus are not limitative of the present disclosure and wherein.

DETAILED DESCRIPTION

Figure 1:
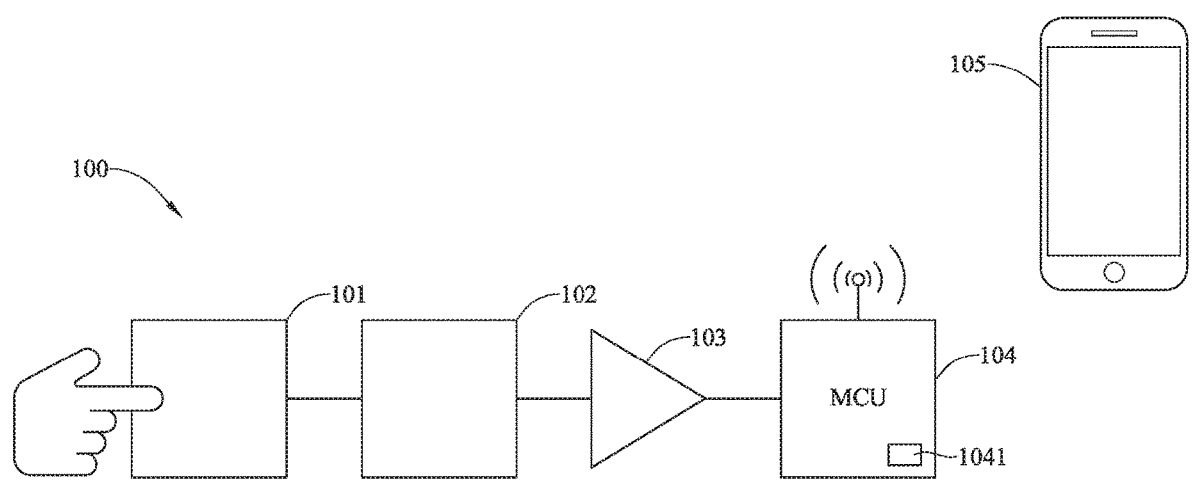
FIG. 1 is a schematic view of a physiological signal sensor according to a first embodiment of the present invention.

Unless defined otherwise, all technical and scientific terms used herein have the same meanings as commonly understood by one of skill in the art to which this disclosure belongs. It will be further understood that terms; such as those defined in commonly used dictionaries, should be interpreted as having a meaning that is consistent with their meaning in the context of the relevant art and the present disclosure, and will not be interpreted in an idealized or overly formal sense unless expressly so defined herein.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Reference is made to FIG. 1, in which a physiological signal sensor according to a first embodiment of the present invention is depicted. As shown in FIG. 1, the physiological signal sensor 100 includes a self-oscillating complementary split-ring resonator (SO-CSRR) element 101, a demodulator 102, a baseband amplifier 103 and a microcontroller (MCU) 104.

In the first embodiment, a user puts his/her finger on the SO-CSRR element 101. The blood flows through the finger causes micro perturbation, and that perturbation further cause the SO-CSRR element 101 to generate a periodic resonant frequency deviation, so that the SO-CSRR element 101 detects a physiological signal through perturbation theory. Next, the SO-CSRR element 101 further, according to injection-locked theory, transforms the physiological signal into a frequency modulated signal and outputs this frequency modulated signal.

The demodulator 102 electrically connects with the SO-CSRR element 101, and the outputted frequency modulated signal is received by the demodulator 102. The demodulator 102 then demodulates the signal to obtain a pulse physiological signal. The pulse physiological signal is the signal measured from finger.

Referring back to FIG. 1, the baseband amplifier 103 electrically connects with the demodulator 102. The baseband amplifier 103 receives the pulse physiological signal, and amplifies the pulse physiological signal. The baseband amplifier 103 then outputs the amplified pulse physiological signal.

The MCU 104 electrically connects with the baseband amplifier 103, and receives the amplified pulse physiological signal. In the present first embodiment, the MCU 104 is embedded with an analog-to-digital converter (ADC converter) 1041. The MCU 104 receives the amplified pulse physiological signal, and the ADC converter 1041 converts this signal into a digital signal. The MCU 104 then transmits the digital signal to an electronic device 105.

In the present first embodiment, the electronic device 105 is a mobile device. The mobile device receives the digital signal and display the information carried in the digital signal on the device's display. Further, the digital signal is wirelessly transmitted to the electronic device 105. However, the transmission is not limited to certain wireless transmission, it can be Bluetooth or Wi-Fi, for different practical demands.

Figure 2:
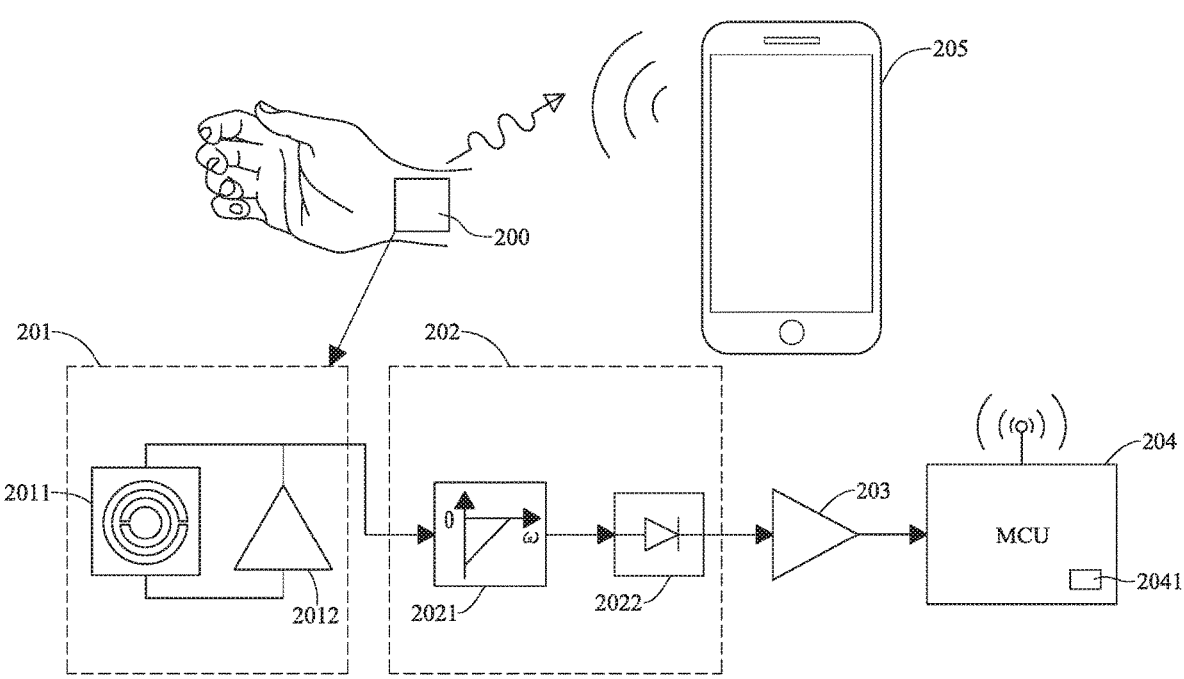
FIG. 2 is a schematic view of a physiological signal sensor according to a second embodiment of the present invention.

Reference is next made to FIG. 2, which is a schematic view of a physiological signal sensor according to a second embodiment of the present invention. In the present embodiment, the physiological signal sensor 100 is placed on the wrist of a user (as shown in FIG. 2). The blood flowing through the wrist causes micro vibrations, and the vibrations further cause the CSRR element 2011 to generate a periodic resonant frequency deviation. It can also be construed that the CSRR element 2011 is capable of measuring a physiological signal through perturbation theory. Afterwords, the SO-CSRR element 201, according to injection-locked theory, transforms the physiology signal into a frequency modulated signal, and further outputs this frequency modulated signal. Further, the SO-CSRR element 201 of the second embodiment includes a complementary split-ring resonator 2011 and a bipolar junction transistor (BJT) radio-frequency (RF) amplifier 2012. In this regard, the SO-CSRR element 201 is configured in a feedback-loop oscillator configuration. It should be noted that the BJT RF amplifier 2012 is only for exemplary purpose and is not meant to limit the scope of the present invention.

The BJT RF amplifier 2012 is used to provide enough gain to satisfy Barkhausen oscillation criteria. That is to say, other circuits that can achieve the similar function as BJT RF amplifier 2012 can also be adopted by the present invention. Moreover, the BJT RF amplifier 2012 is applied with a 3.3V bias voltage, and the current is 12 mA, in the present embodiment.

An amplitude demodulation element 202 electrically connects with the SO-CSRR element 201, and the above mentioned output frequency modulated signal is received by the amplitude demodulation element 202. The modulated signal is demodulated by the amplitude demodulation element 202 and a pulse physiological signal is then obtained. This pulse physiological signal is the physiological signal measured from the wrist. As shown in FIG. 2, the amplitude demodulation element 202 is implemented by a microwave differentiator 2021 and an envelope detector 2022. To be more specific, the amplitude demodulation element 202 transformed a frequency modulated signal it received into an amplitude modulated signal, and to retrieve the wrist pulse signal from the amplitude variation of the amplitude modulated signal.

The baseband amplifier 203 electrically connects with the amplitude demodulation element 202. The baseband amplifier 203 receives the pulse physiological signal, and amplifies the received pulse physiological signal. The baseband amplifier 203 then outputs the amplified pulse physiological signal.

The microcontroller (MCU) 204 electrically connects the baseband amplifier 203 to receive the amplified pulse physiological signal. In the present second embodiment, the MCU 204 is embedded with an analog-to-digital converter (ADC converter) 2041. The MCU 204 receives the amplified pulse physiological signal, and the ADC converter 2041 coverts the signal into a digital signal. The MCU 204 then, through wireless transmission, transmits the digital to an electronic device 205.

In the present embodiment, the electronic device 205 is a mobile tablet PC. The mobile tablet PC 205, after receiving the digital signal, display the information contained in the digital signal on its screen. The wireless transmission is not limited to any form of transmission, it could be, but not limited to, Bluetooth or Wi-Fi.

Figure 3:
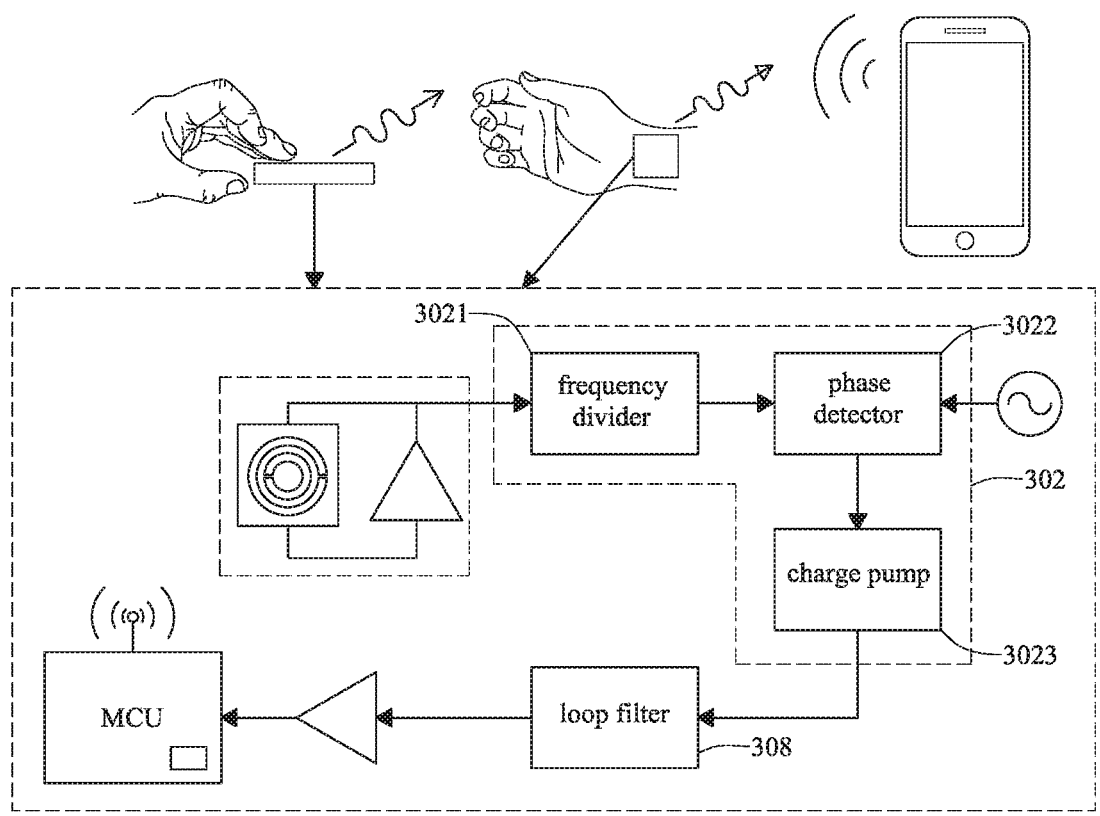
FIG. 3 is a schematic view of a physiological signal sensor according to a third embodiment of the present invention.

Reference is next made to FIG. 3, which is a schematic view of a physiological signal sensor according to a third embodiment of the present invention. In the third embodiment, the frequency demodulation element 302 includes a frequency divider 3021, a phase detector 3022 and a charge pump 3023. The frequency demodulation element 302 receives a reference signal. Further, the signal outputted by the frequency demodulation element 302 is processed by a loop filter 308 before being baseband amplifying.

According to the physiological signal sensor provided by the present invention, it is based on perturbation theory and injection-locked theory, and possesses high sensitivity. Due to its high sensitivity, the physiological signal sensor can be used to measure many kinds of physiological signals, such as wrist pulse signal or finger pulse signal. As such, the physiological signal sensor of the present invention can be applied in various wearable devices, and is capable of facilitating health care industry developments. Furthermore, since the present physiological signal sensor is based on both perturbation theory and injection-locked theory, it can also be referred to as a perturbation-injection-locked sensor, or PIL sensor.

Figure 4A:
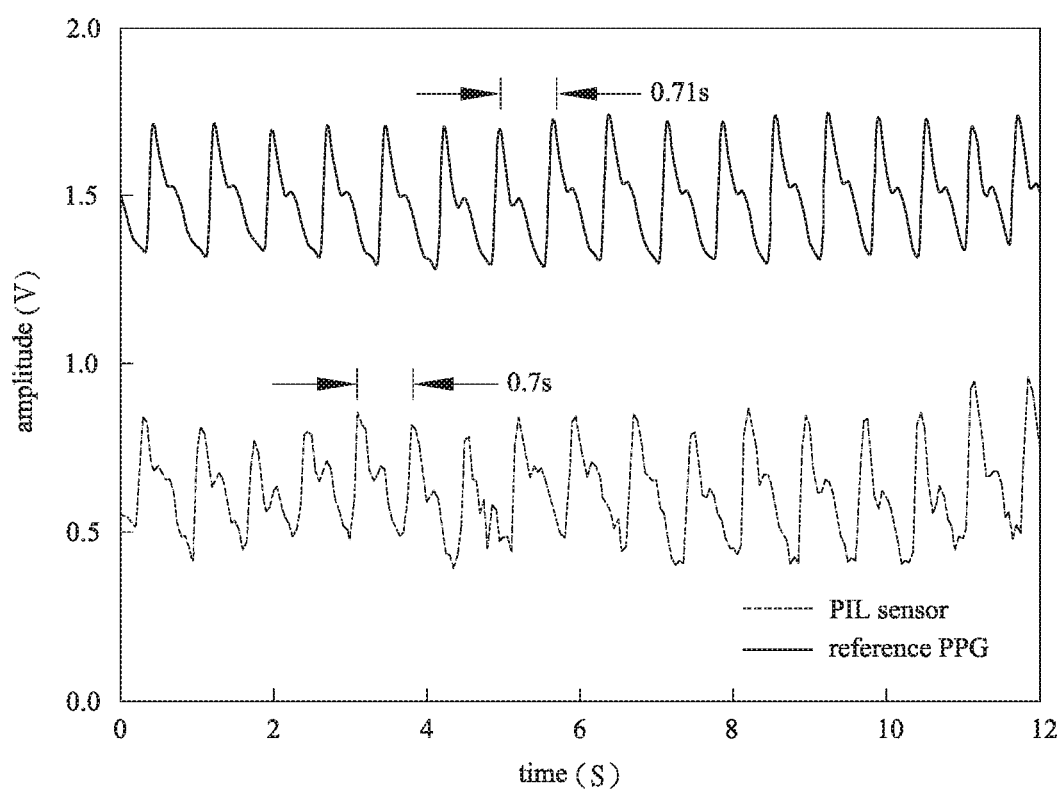
FIG. 4(a) is an experimental simulation view illustrating the second embodiment of the present invention (time domain)
Figure 4B:
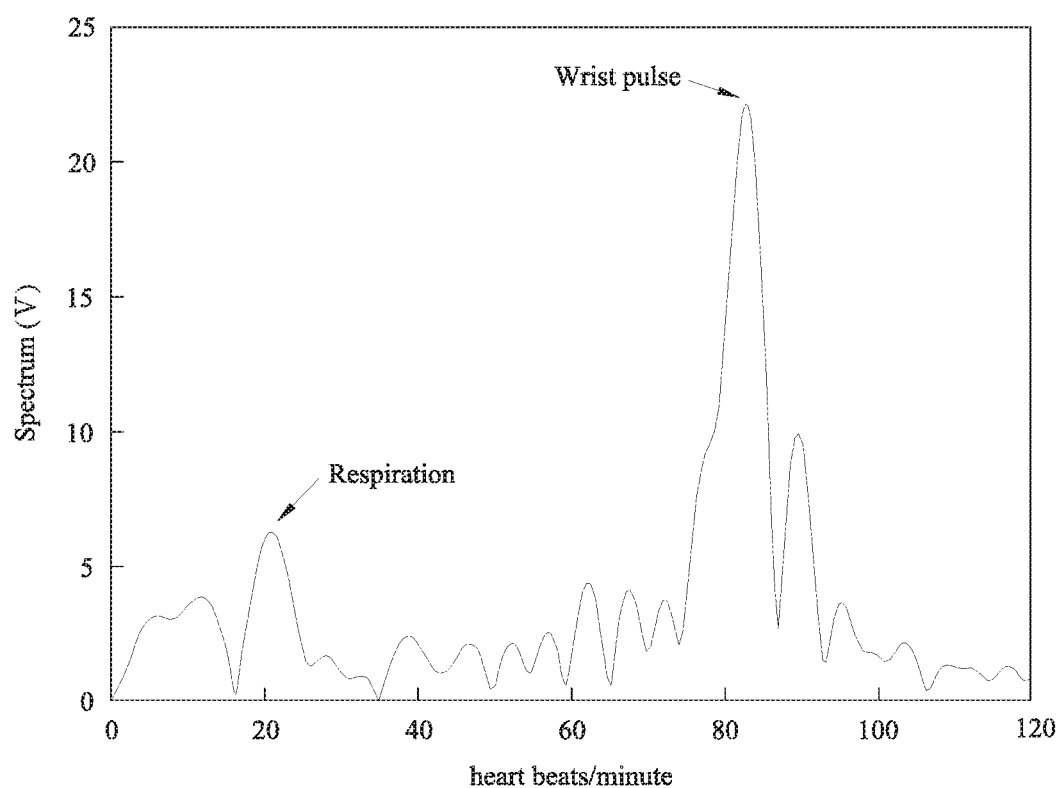
FIG. 4(b) is an experimental simulation view illustrating the second embodiment of the present invention (frequency domain).

Reference is next made to FIGS. 4(a)-4(b). FIG. 4(a) is an experimental simulation view illustrating the second embodiment of the present invention (time domain), and FIG. 4(b) is an experimental simulation view illustrating the second embodiment of the present invention (frequency domain). In FIG. 4(a), the dot lines represent the experimental simulation of the PIL sensor of the present invention, and the real Ines represent the experimental simulation of photoplethysmography (PPG) sensor. Form the comparison, it can be seen that the PIL sensor performs as good as PPG sensor, but the PIL sensor improves on some disadvantages exhibited by PPG sensor (e.g., wearable device being wore too tight or too loose, ambient light, skin property and etc.)

According to FIG. 4(b), there are two peaks in the figure. The two peaks respectively represent respiration rate of 20.8 beats per minute (20.8 beat/min) and 82.8 beats per minute (82.8 beat/min). Therefore, the PIL sensor of the present invention can simultaneously measure respiration rate and wrist pulse.

With respect to the above description then, it is to be realized that the optimum dimensional relationships for the parts of the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present disclosure.

What is claimed is:

1. A physiological signal sensor, comprising:
    a self-oscillating complementary split-ring resonator (SO-CSRR) element, configured to detect a physiological signal and output a modulated signal;
    a demodulator electrically connected with the SO-CSRR element;
    a baseband amplifier electrically connected with the demodulator; and
    a microcontroller (MCU) electrically connected with the baseband amplifier;
    wherein the demodulator receives the modulated signal and outputs a pulse physiological signal, the baseband amplifier receives the pulse physiological signal and outputs an amplified pulse physiological signal, and the MCU receives the amplified pulse physiological signal and outputs a digital signal.

2. The physiological signal sensor of claim 1, wherein the SO-CSRR element includes a complementary split-ring resonator and a bipolar transistor radio frequency amplifier.

3. The physiological signal sensor of claim 1, wherein the demodulator is an amplitude demodulator.

4. The physiological signal sensor of claim 3, wherein the demodulator includes a microwave differentiator and an envelope detector.

5. The physiological signal sensor of claim 1, wherein the demodulator is a frequency demodulator.

6. The physiological signal sensor of claim 5, wherein the demodulator includes a frequency divider, a phase detector and a charge pump.

7. The physiological signal sensor of claim 6, wherein the physiological signal sensor further includes a loop filter.

8. The physiological signal sensor of claim 1, wherein the MCU further includes an analog-to-digital converter (ADC).

9. The physiological signal sensor of claim 1, wherein the digital signal is wirelessly transmitted, and is received by an electronic device.

10. The physiological signal sensor of claim 1, wherein the physiological signal is measured from a wrist or a finger.

* * * * *